United States Patent
Gough et al.

[11] Patent Number: 6,059,780
[45] Date of Patent: *May 9, 2000

[54] MULTIPLE ANTENNA ABLATION APPARATUS AND METHOD WITH COOLING ELEMENT

[75] Inventors: Edward J. Gough, Menlo Park; Alan A. Stein, Moss Beach, both of Calif.

[73] Assignee: Rita Medical Systems, Inc., Mountain View, Calif.

[*] Notice: This patent is subject to a terminal disclaimer.

[21] Appl. No.: 08/964,034

[22] Filed: Nov. 4, 1997

Related U.S. Application Data

[63] Continuation-in-part of application No. 08/616,928, Mar. 15, 1996, Pat. No. 5,810,804, which is a continuation-in-part of application No. 08/515,379, Aug. 15, 1995, Pat. No. 5,683,384.

[51] Int. Cl.[7] ..................................................... A61B 18/18
[52] U.S. Cl. .............................. 606/42; 606/41; 607/101; 607/105
[58] Field of Search ........................... 606/41, 42, 45–50; 607/100–105; 604/21, 22

[56] References Cited

U.S. PATENT DOCUMENTS

| | | |
|---|---|---|
| Re. 32,057 | 12/1985 | Leveen . |
| Re. 32,066 | 1/1986 | Leveen . |
| Re. 34,086 | 10/1992 | George . |
| 3,474,777 | 10/1969 | Figge et al. . |
| 3,834,392 | 9/1974 | Lampman et al. . |
| 3,858,586 | 1/1975 | Lessen . |
| 3,987,795 | 10/1976 | Morrison, Jr. . |
| 3,991,770 | 11/1976 | Leveen . |
| 4,011,872 | 3/1977 | Komiya . |
| 4,016,881 | 4/1977 | Rioux et al. . |
| 4,016,886 | 4/1977 | Doss . |
| 4,026,301 | 5/1977 | Friedman et al. . |
| 4,033,351 | 7/1977 | Hetzel . |
| 4,043,342 | 8/1977 | Morrison, Jr. . |
| 4,074,718 | 2/1978 | Morrison, Jr. . |
| 4,080,959 | 3/1978 | Leveen . |
| 4,085,756 | 4/1978 | Weaver . |

(List continued on next page.)

FOREIGN PATENT DOCUMENTS

| | | |
|---|---|---|
| 0 370 890 | 5/1990 | European Pat. Off. . |
| 0 462 302 | 12/1991 | European Pat. Off. . |
| 0 472 368B1 | 2/1992 | European Pat. Off. . |
| 0 502 268 | 9/1992 | European Pat. Off. . |
| 0 519 415 | 12/1992 | European Pat. Off. . |
| 0 608 609 | 8/1994 | European Pat. Off. . |
| WO 92/10142 | 6/1992 | WIPO . |
| WO 94/04220 | 3/1994 | WIPO . |
| WO 94/10925 | 5/1994 | WIPO . |
| WO 94/11059 | 5/1994 | WIPO . |
| WO 94/17856 | 8/1994 | WIPO . |
| WO 94/25110 | 11/1994 | WIPO . |
| WO 94/26178 | 11/1994 | WIPO . |
| WO 95/19142 | 7/1995 | WIPO . |
| WO 95/25471 | 9/1995 | WIPO . |
| WO 96/04860 | 2/1996 | WIPO . |
| WO 96/29946 | 10/1996 | WIPO . |
| WO 97/06739 | 2/1997 | WIPO . |

*Primary Examiner*—Michael Peffley
*Attorney, Agent, or Firm*—Wilson Sonsini Goodrich & Rosati

[57] ABSTRACT

An ablation apparatus includes a handpiece, an electrode extending from a handpiece distal end, a probe, a thermal sensor and an energy source. The electrode includes a distal end and a lumen, a cooling medium inlet conduit and a cooling medium exit conduit. Both conduits extend through the electrode lumen to an electrode distal end. A sidewall port, isolated from a cooling medium flowing in the inlet and outlet conduits, is formed in the electrode. The probe is at least partially positionable in the electrode lumen and configured to be advanced and retracted in and out of the sidewall aperture. The thermal sensor is supported by the probe. The electrode is coupled to an energy source.

36 Claims, 5 Drawing Sheets

U.S. PATENT DOCUMENTS

| | | |
|---|---|---|
| 4,095,602 | 6/1978 | Leveen . |
| 4,119,102 | 10/1978 | Leveen . |
| 4,121,592 | 10/1978 | Whalley . |
| 4,140,130 | 2/1979 | Storm, III . |
| 4,154,246 | 5/1979 | Leveen . |
| 4,230,129 | 10/1980 | Leveen . |
| 4,237,898 | 12/1980 | Whalley . |
| 4,269,174 | 5/1981 | Adair . |
| 4,285,346 | 8/1981 | Armitage . |
| 4,289,135 | 9/1981 | Nordensrom et al. . |
| 4,290,435 | 9/1981 | Waggott . |
| 4,303,636 | 12/1981 | Gordon . |
| 4,331,654 | 5/1982 | Morris . |
| 4,337,760 | 7/1982 | Rubin . |
| 4,345,588 | 8/1982 | Widder et al. . |
| 4,346,715 | 8/1982 | Gammell . |
| 4,375,220 | 3/1983 | Matvias . |
| 4,409,993 | 10/1983 | Furihata . |
| 4,411,266 | 10/1983 | Cosman . |
| 4,418,692 | 12/1983 | Guay . |
| 4,461,283 | 7/1984 | Doi . |
| 4,506,680 | 3/1985 | Stokes . |
| 4,512,762 | 4/1985 | Spears . |
| 4,524,770 | 6/1985 | Orandi . |
| 4,532,924 | 8/1985 | Auth et al. . |
| 4,545,368 | 10/1985 | Rand et al. . |
| 4,562,838 | 1/1986 | Walker . |
| 4,565,200 | 1/1986 | Cosman . |
| 4,574,782 | 3/1986 | Borrelli et al. . |
| 4,583,556 | 4/1986 | Hines et al. . |
| 4,586,490 | 5/1986 | Katz . |
| 4,601,296 | 7/1986 | Yerushalmi . |
| 4,648,892 | 3/1987 | Kittrell et al. . |
| 4,652,257 | 3/1987 | Chang . |
| 4,658,819 | 4/1987 | Harris et al. . |
| 4,660,571 | 4/1987 | Hess et al. . |
| 4,662,359 | 5/1987 | Gordon . |
| 4,676,258 | 6/1987 | Inokuchi et al. . |
| 4,690,130 | 9/1987 | Mirell . |
| 4,692,139 | 9/1987 | Stiles . |
| 4,709,701 | 12/1987 | Weber . |
| 4,753,248 | 6/1988 | Engler et al. . |
| 4,763,671 | 8/1988 | Goffinet . |
| 4,776,086 | 10/1988 | Kasevich et al. . |
| 4,800,899 | 1/1989 | Elliott . |
| 4,813,429 | 3/1989 | Eshel et al. . |
| 4,818,542 | 4/1989 | Deluca et al. . |
| 4,823,791 | 4/1989 | D'Amelio et al. . |
| 4,823,793 | 4/1989 | Angulo et al. . |
| 4,825,880 | 5/1989 | Stauffer et al. . |
| 4,838,265 | 6/1989 | Cosman et al. . |
| 4,846,196 | 7/1989 | Wiksell et al. . |
| 4,860,744 | 8/1989 | Johnson et al. . |
| 4,862,887 | 9/1989 | Weber et al. . |
| 4,881,543 | 11/1989 | Trembly et al. . |
| 4,887,614 | 12/1989 | Shirakami et al. . |
| 4,907,589 | 3/1990 | Cosman . |
| 4,920,978 | 5/1990 | Colvin . |
| 4,931,047 | 6/1990 | Broadwin et al. . |
| 4,940,064 | 7/1990 | Desai . |
| 4,945,912 | 8/1990 | Langberg . |
| 4,947,842 | 8/1990 | Marchosky et al. . |
| 4,950,267 | 8/1990 | Ishihara et al. . |
| 4,962,761 | 10/1990 | Golden . |
| 4,963,364 | 10/1990 | Fox et al. . |
| 4,966,604 | 10/1990 | Reiss . |
| 4,976,680 | 12/1990 | Hayman et al. . |
| 4,976,711 | 12/1990 | Parins et al. . |
| 4,983,159 | 1/1991 | Rand . |
| 4,985,022 | 1/1991 | Fearnot et al. . |
| 4,989,601 | 2/1991 | Marchosky et al. . |
| 5,003,991 | 4/1991 | Takayama et al. . |
| 5,007,908 | 4/1991 | Rydell . |
| 5,009,656 | 4/1991 | Reimels . |
| 5,010,897 | 4/1991 | Leveen . |
| 5,011,483 | 4/1991 | Sleister . |
| 5,013,312 | 5/1991 | Parins et al. . |
| 5,015,227 | 5/1991 | Broadwin et al. . |
| 5,016,615 | 5/1991 | Driller et al. . |
| 5,026,959 | 6/1991 | Ito et al. . |
| 5,047,027 | 9/1991 | Rydell . |
| 5,055,100 | 10/1991 | Olsen . |
| 5,057,107 | 10/1991 | Parins et al. . |
| 5,059,199 | 10/1991 | Okada et al. . |
| 5,067,952 | 11/1991 | Gudov et al. . |
| 5,071,419 | 12/1991 | Rydell et al. . |
| 5,078,717 | 1/1992 | Parins et al. . |
| 5,080,660 | 1/1992 | Buelna . |
| 5,083,565 | 1/1992 | Parins . |
| 5,084,001 | 1/1992 | Van't Hooft et al. . |
| 5,084,045 | 1/1992 | Helenowski . |
| 5,085,659 | 2/1992 | Rydell . |
| 5,099,756 | 3/1992 | Franconi et al. . |
| 5,100,423 | 3/1992 | Fearnot . |
| 5,115,818 | 5/1992 | Holleman et al. . |
| 5,119,832 | 6/1992 | Xavier . |
| 5,122,137 | 6/1992 | Lennox . |
| 5,125,928 | 6/1992 | Parins et al. . |
| 5,128,147 | 7/1992 | Leveen et al. . |
| 5,156,151 | 10/1992 | Imran . |
| 5,167,626 | 12/1992 | Casper et al. . |
| 5,169,396 | 12/1992 | Dowlatshahi et al. . |
| 5,170,789 | 12/1992 | Narayan et al. . |
| 5,170,805 | 12/1992 | Kensey et al. . |
| 5,178,620 | 1/1993 | Eggers et al. . |
| 5,183,455 | 2/1993 | Hayman et al. . |
| 5,190,517 | 3/1993 | Zieve et al. . |
| 5,190,539 | 3/1993 | Fletcher et al. . |
| 5,190,541 | 3/1993 | Abele . |
| 5,190,766 | 3/1993 | Ishihara . |
| 5,197,466 | 3/1993 | Marchosky et al. . |
| 5,197,963 | 3/1993 | Parins . |
| 5,197,964 | 3/1993 | Parins . |
| 5,203,353 | 4/1993 | Easley et al. . |
| 5,203,782 | 4/1993 | Gudov et al. . |
| 5,205,289 | 4/1993 | Hardy et al. . |
| 5,207,675 | 5/1993 | Canady . |
| 5,215,103 | 6/1993 | Desai . |
| 5,217,458 | 6/1993 | Parins . |
| 5,222,953 | 6/1993 | Dowlatshahi . |
| 5,236,410 | 8/1993 | Granov et al. . |
| 5,236,424 | 8/1993 | Imran . |
| 5,246,438 | 9/1993 | Langberg . |
| 5,249,585 | 10/1993 | Turner et al. . |
| 5,251,645 | 10/1993 | Fenn . |
| 5,252,922 | 10/1993 | Larson, III . |
| 5,257,451 | 11/1993 | Edwards et al. . |
| 5,258,006 | 11/1993 | Rydell et al. . |
| 5,259,394 | 11/1993 | Bens . |
| 5,259,395 | 11/1993 | Li . |
| 5,267,994 | 12/1993 | Gentelia et al. . |
| 5,273,535 | 12/1993 | Edwards et al. . |
| 5,275,162 | 1/1994 | Edwards et al. . |
| 5,277,696 | 1/1994 | Hagen . |
| 5,281,213 | 1/1994 | Milder et al. . |
| 5,281,217 | 1/1994 | Edwards et al. . |
| 5,281,218 | 1/1994 | Imran . |
| 5,282,797 | 2/1994 | Chess . |
| 5,286,253 | 2/1994 | Fucci . |
| 5,290,286 | 3/1994 | Parins . |
| 5,293,869 | 3/1994 | Edwards et al. . |
| 5,295,955 | 3/1994 | Rosen et al. . |

| | | | | | |
|---|---|---|---|---|---|
| 5,300,068 | 4/1994 | Rosar et al. . | 5,458,596 | 10/1995 | Lax et al. . |
| 5,300,069 | 4/1994 | Hunsberger et al. . | 5,458,597 | 10/1995 | Edwards et al. . |
| 5,300,099 | 4/1994 | Rudie . | 5,462,521 | 10/1995 | Brucker et al. . |
| 5,304,214 | 4/1994 | Deford et al. . | 5,470,308 | 11/1995 | Edwards et al. . |
| 5,309,910 | 5/1994 | Edwards et al. . | 5,470,309 | 11/1995 | Edwards et al. . |
| 5,313,943 | 5/1994 | Houser et al. . | 5,471,982 | 12/1995 | Edwards et al. . |
| 5,314,466 | 5/1994 | Stern et al. . | 5,472,441 | 12/1995 | Edwards et al. . |
| 5,322,503 | 6/1994 | Desai . | 5,484,400 | 1/1996 | Edwards et al. . |
| 5,328,467 | 7/1994 | Edwards et al. . | 5,486,161 | 1/1996 | Lax et al. . |
| 5,334,193 | 8/1994 | Nardella ................................ 606/41 | 5,500,012 | 3/1996 | Brucker et al. . |
| 5,334,206 | 8/1994 | Daikuzono . | 5,505,730 | 4/1996 | Edwards . |
| 5,336,222 | 8/1994 | Durgin, Jr. et al. . | 5,507,743 | 4/1996 | Edwards et al. . |
| 5,342,357 | 8/1994 | Nardella . | 5,509,419 | 4/1996 | Edwards et al. . |
| 5,348,554 | 9/1994 | Imran et al. ............................. 606/41 | 5,514,130 | 5/1996 | Baker . |
| 5,354,296 | 10/1994 | Turkel . | 5,514,131 | 5/1996 | Edwards . |
| 5,363,861 | 11/1994 | Edwards et al. . | 5,520,684 | 5/1996 | Imran . |
| 5,365,926 | 11/1994 | Desai . | 5,531,676 | 7/1996 | Edwards et al. . |
| 5,366,490 | 11/1994 | Edwards et al. . | 5,531,677 | 7/1996 | Lundquist et al. . |
| 5,368,592 | 11/1994 | Stern et al. . | 5,536,240 | 7/1996 | Edwards et al. . |
| 5,370,675 | 12/1994 | Edwards et al. . | 5,536,267 | 7/1996 | Edwards et al. . |
| 5,370,678 | 12/1994 | Edwards et al. . | 5,540,655 | 7/1996 | Edwards et al. . |
| 5,383,876 | 1/1995 | Nardella . | 5,542,915 | 8/1996 | Edwards et al. . |
| 5,383,917 | 1/1995 | Desai et al. . | 5,542,916 | 8/1996 | Hirsch et al. . |
| 5,385,544 | 1/1995 | Edwards et al. . | 5,542,928 | 8/1996 | Evans et al. . |
| 5,397,339 | 3/1995 | Desai . | 5,545,161 | 8/1996 | Imran . |
| 5,398,683 | 3/1995 | Edwards et al. . | 5,545,171 | 8/1996 | Sharkey et al. . |
| 5,401,272 | 3/1995 | Perkins . | 5,545,193 | 8/1996 | Fleischman et al. . |
| 5,403,311 | 4/1995 | Abele et al. . | 5,546,267 | 8/1996 | Frederiksen et al. . |
| 5,405,346 | 4/1995 | Grundy et al. . | 5,548,597 | 8/1996 | Edwards et al. . |
| 5,409,453 | 4/1995 | Lundquist et al. . | 5,549,108 | 8/1996 | Edwards et al. . |
| 5,411,025 | 5/1995 | Webster, Jr. . | 5,549,644 | 8/1996 | Lundquist et al. . |
| 5,417,687 | 5/1995 | Nardella . | 5,554,110 | 9/1996 | Edwards et al. . |
| 5,421,819 | 6/1995 | Edwards et al. . | 5,556,377 | 9/1996 | Rosen et al. . |
| 5,423,807 | 6/1995 | Milder . | 5,558,672 | 9/1996 | Edwards et al. . |
| 5,423,808 | 6/1995 | Edwards et al. . | 5,558,673 | 9/1996 | Edwards et al. . |
| 5,423,811 | 6/1995 | Imran et al. . | 5,560,358 | 10/1996 | Arnold et al. . |
| 5,433,708 | 7/1995 | Nichols et al. . | 5,562,703 | 10/1996 | Desai . |
| 5,435,805 | 7/1995 | Edwards et al. . | 5,599,345 | 2/1997 | Edwards et al. . |
| 5,437,662 | 8/1995 | Nardella . | 5,599,346 | 2/1997 | Edwards et al. . |
| 5,437,664 | 8/1995 | Cohen et al. . | 5,609,151 | 3/1997 | Mulier et al. . |
| 5,456,662 | 10/1995 | Edwards et al. . | 5,620,481 | 4/1997 | Desai et al. . |
| 5,456,682 | 10/1995 | Edwards et al. . | | | |

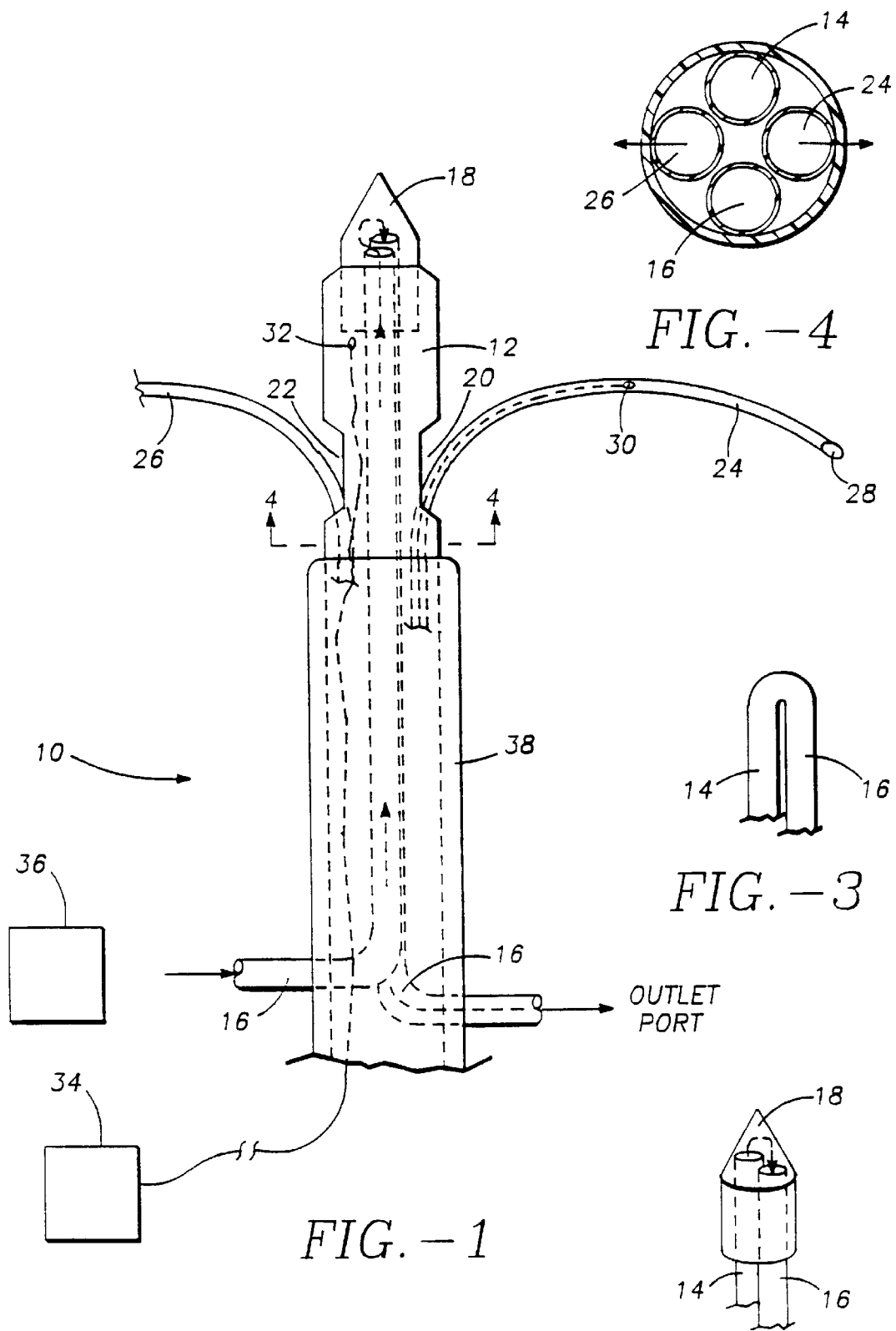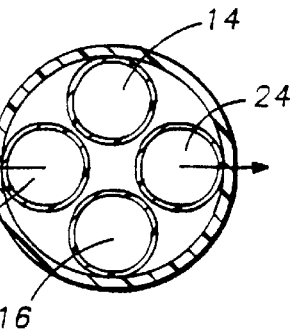

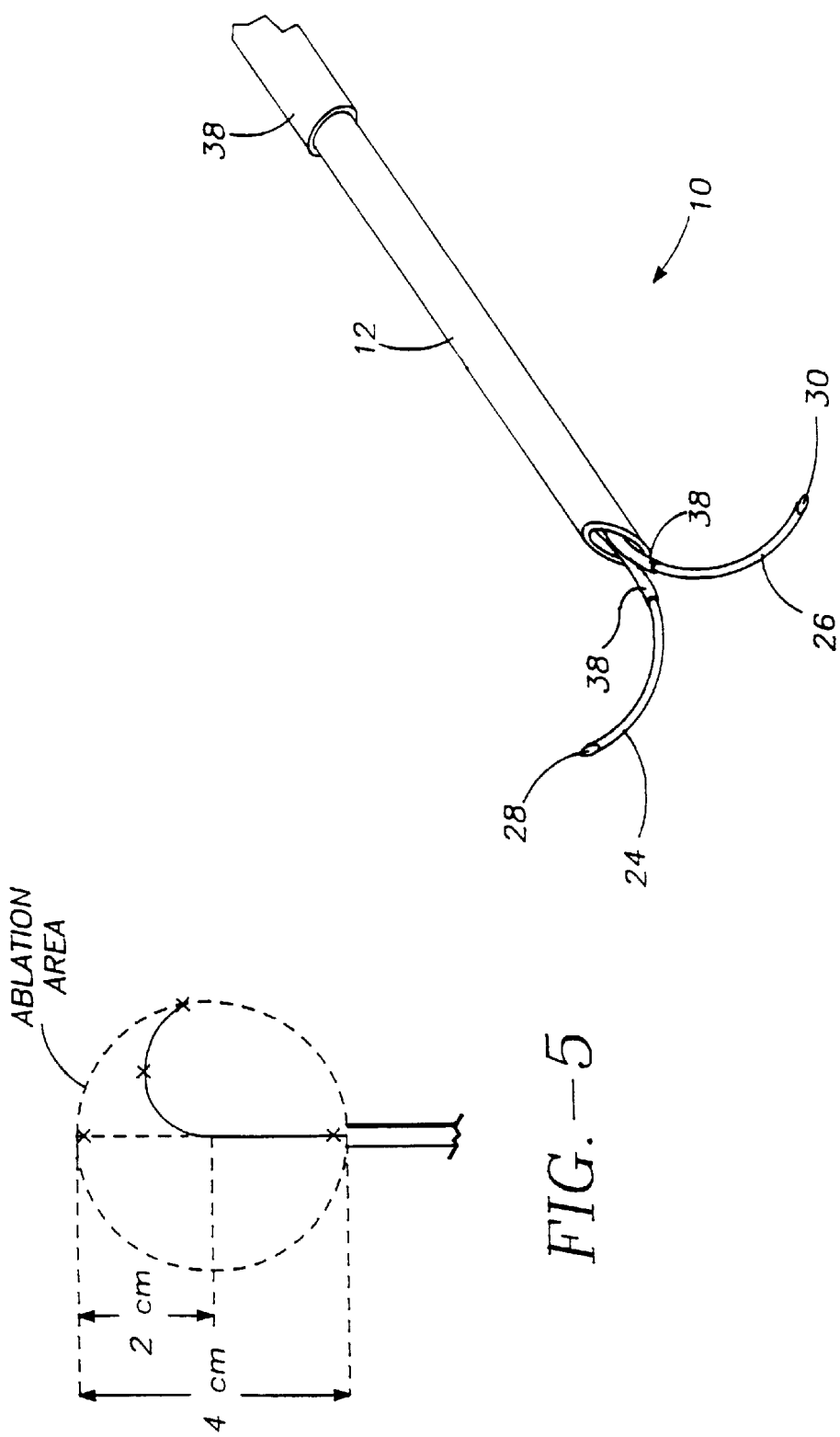

MULTIPLE ANTENNA ABLATION APPARATUS AND METHOD WITH COOLING ELEMENT

Reference to Related Application

This application is a continuation-in-part of U.S. patent application No. 08/616,928, filed Mar. 15, 1996, now U.S. Pat. No. 5,810,804, which is a continuation-in-part of 08/515,379, filed Aug. 15, 1995, now U.S. Pat. No. 5,683,384, both of which are incorporated herein by reference.

BACKGROUND OF THE INVENTION

1. Field of the Invention

This invention relates generally to an ablation apparatus with an internally cooled electrode, and more particularly to an electrode with a closed looped cooling device positioned in an electrode lumen, and an electrode sidewall port isolated from a cooling medium flowing through the closed looped cooling device.

2. Description of the Related Art

Current open procedures for treatment of tumors are extremely disruptive and cause a great deal of damage to healthy tissue. During the surgical procedure, the physician must exercise care in not cutting the tumor in a manner that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the skin.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

RF ablation electrodes tend to impede out when used at higher power levels. The tissue adjacent to the electrode surface tends to char. There have been numerous cooled electrodes. Examples of cooled electrodes are found in U.S. Pat. Nos.: 4,290,435; 4,140,130; 4,881,543; 5,334,193; 5,342,357; 5,348,554; 5,423,811; 5,423,807; 5,437,662; and 5,462,521.

There is a need for an ablation apparatus with a closed loop cooling device positioned in an electrode lumen. There is a further need for an ablation apparatus with a closed loop cooling device positioned in an electrode lumen, and an electrode sidewall port isolated from the closed loop cooling device and suitable for the introduction of probes and/or infusion solutions into a selected tissue site.

SUMMARY OF THE INVENTION

Accordingly, it is an object of the invention to provide an ablation apparatus and method with an ablation electrode that does not impede out.

Another object of the invention is to provide an ablation apparatus and method with a cooled ablation electrode.

Yet another object of the invention is to provide an ablation apparatus and method with a closed loop cooled ablation electrode.

A further object of the invention is to provide an ablation apparatus and method with a closed loop cooled ablation electrode and an electrode sidewall port that is isolated from a cooling medium flowing through the ablation electrode.

Still another object of the invention is to provide an ablation apparatus and method with a closed loop cooled ablation electrode, an electrode sidewall port isolated from a cooling medium flowing through the ablation electrode and a probe with a sensor that is advanced in and out of the sideport.

Another object of the invention is to provide an ablation apparatus and method with a closed loop cooled ablation electrode, an electrode sidewall port isolated from a cooling medium flowing through the ablation electrode and an infusion medium introduced into a selected tissue site through the sidewall port.

These and other objectives are achieved in an ablation apparatus that has a handpiece, an electrode extending from a handpiece distal end, a probe, a thermal sensor and an energy source. The electrode includes a distal end, a lumen, a cooling medium inlet conduit and a cooling medium exit conduit. Both conduits extend through the electrode lumen to an electrode distal end. A sidewall port, isolated from a cooling medium flowing in the inlet and outlet conduits, is formed in the electrode. The probe is at least partially positionable in the electrode lumen and configured to be advanced and retracted in and out of the sidewall port. The thermal sensor is supported by the probe. The electrode is coupled to an energy source.

The present invention is also a method for creating an ablation volume in a selected tissue mass. An ablation device is provided that has a handpiece, an electrode, a probe and a thermal sensor supported by the probe. The electrode includes a distal end, a lumen, a cooling medium inlet conduit coupled to a cooling medium outlet conduit which both extend through the electrode lumen to the electrode's distal end. A sidewall port is formed in a sidewall of the electrode and is isolated from a cooling medium flowing through the electrode. The electrode is inserted into the selected tissue mass. At least a portion of the probe is positioned in the electrode after the electrode has been inserted into the selected tissue mass. A distal end of the probe is advanced from the aperture into the selected tissue. At least a portion of an electrode ablation surface is cooled. Electromagnetic energy is delivered from the electrode to the selected tissue mass. Temperature is measured at a site in the selected tissue mass, and an ablation volume is created.

As electromagnetic energy, including but not limited to RF, is delivered to the selected tissue site, the tissue interface adjacent to the electrode can begin to char and conductivity through the tissue decreases. With a cooling medium the tissue interface remains at a temperature suitable for the delivery of electromagnetic energy to the periphery of the desired ablation site. While a cooling medium is flowing through the electrode, one or more probes, with associated sensors, are deployed into the desired ablation site. The ablation is monitored and controlled. Sensors can be positioned not only at the distal ends of the probes but also at intermediate positions. This permits monitoring of the ablation process between the electrode and the periphery of the targeted ablation volume.

BRIEF DESCRIPTION OF THE FIGURES

FIG. 1 is a cross-sectional view of the ablation apparatus of the present invention illustrating an electrode with a lumen, a cooling medium inlet conduit, a cooling medium outlet conduit and two probes extending from sidewall ports formed in the lumen.

FIG. 2 is a cross-sectional view of the closed loop distal end of the two cooling medium conduits of FIG. 1.

FIG. 3 is a cross-sectional view of another embodiment of the closed loop distal end of the two cooling medium conduits.

FIG. 4 is a cross-sectional of FIG. 1 taken along the lines 4—4.

FIG. 5 illustrates the creation of a 4 cm spherical ablation volume, with one sensor positioned at the periphery of the ablation volume, and a second sensor positioned on the probe midpoint between the electrode and the distal end of the probe.

FIG. 6 is a perspective view of the ablation apparatus of the present invention illustrating two probes extending from a distal end of the electrode.

DETAILED DESCRIPTION

Figure 8:
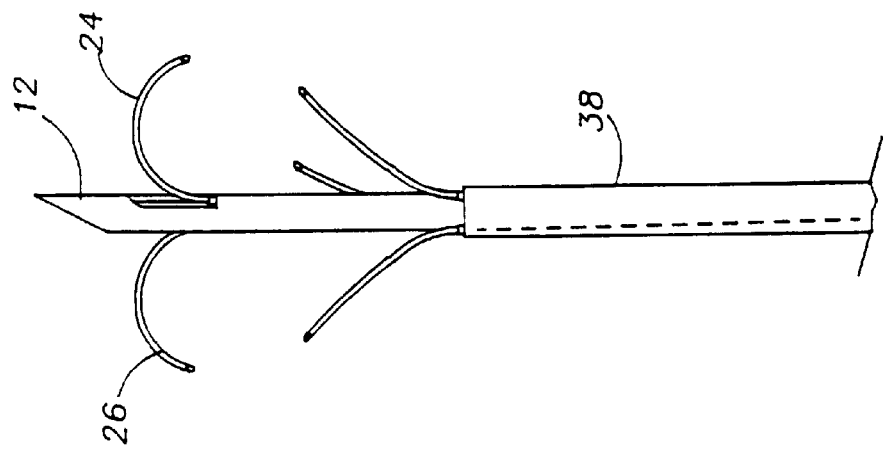
FIG. 8 is a perspective view of the ablation apparatus of the present invention illustrating the deployment of four probes from the electrode.

As shown in FIG. 1, an ablation apparatus 10 includes a handpiece 11, an electrode 12, a cooling medium inlet conduit 16, a cooling medium outlet conduit 16 and a cap 18, with tapered distal end, that create a closed loop cooling system. Handpiece can be an insulated portion of electrode 12. A variety of different cooling mediums can be used including but not limited to gas, cooled air, refrigerated air, compressed air, Freon, water, alcohol, saline and the like. A first sidewall port 20 is formed in a sidewall of electrode 12. A second sidewall port 22 may also be included. First and second sidewall ports can be windows formed in electrode 12 which create a mechanical weak spot in electrode 12. A first probe 24 is positionable in an electrode lumen before or following introduction of electrode 12 in a selected tissue mass. First probe 24 capable of being advanced and retracted in and out of first sidewall port 20. An optional second probe 26 is also positioned in the electrode lumen and is capable of being advanced and retracted to a selected tissue ablation side through second sidewall port 22.

Electrode 12 has an exterior ablation energy delivery surface which delivers electromagnetic energy to the selected tissue ablation mass, and may have a tapered or sharpened distal end. For the ablation of tumors, electrode 12 can have an exterior ablation energy delivery surface length of 0.25 inches or less, and an outer diameter for electrode 12 of about 0.072 inches or less.

Each probe 24 and 26 can be formed of a variety of materials, including but not limited to stainless steel, shaped memory metals and the like. The size of probes 24 and 26 vary depending on the medical application. For the treatment of tumors, probes 24 and 26 have a length extending from the sidewall ports into tissue of 3 cm or less. A first sensor 28 can be supported by probe 24 on an interior or exterior surface. First sensor 28 is preferably positioned at a distal end of probe 24. A second sensor 30 may be positioned on probe 24 somewhere intermediate between an exterior surface of electrode 12 and the distal end of probe 24. Preferably, second sensor 30 is located at a position where it can sense temperature at a midpoint in a selected tissue ablation volume. Second sensor 30 is useful to determine if probe 24 has encountered an obstruction, such as a blood vessel, to the ablation process. If first sensor 28 measures a higher temperature than second sensor 30, then this can indicate that second sensor 30 is close to a circulatory vessel. When this occurs, ablation energy is carried away by the vessel. Similarly, second probe 26 can also include one or more sensors. A third sensor 32 can be positioned at an exterior surface of electrode 12.

Sensors 28, 30 and 32 permit accurate measurement of temperature at a tissue site in order to determine, (i) the extent of ablation, (ii) the amount of ablation, (iii) whether or not further ablation is needed and (iv) the boundary or periphery of the ablated mass. Further, sensors 28, 30 and 32 prevent non-targeted tissue from being destroyed or ablated.

Sensors 28, 30 and 32 are of conventional design, including but not limited to thermistors, thermocouples, resistive wires, and the like. Suitable thermal sensors 24 include a T type thermocouple with copper constantene, J type, E type, K type, fiber optics, resistive wires, thermocouple IR detectors, and the like. Sensors 28, 30 and 32 need not be thermal sensors.

Sensors 28, 30 and 32 measure temperature and/or impedance to permit monitoring and a desired level of ablation to be achieved without destroying too much tissue. This reduces damage to tissue surrounding the targeted mass to be ablated. By monitoring the temperature at various points within the interior of the selected tissue mass, a determination of the selected tissue mass periphery can be made, as well as a determination of when ablation is complete. If at any time sensor 28, 30 or 32 determines that a desired ablation temperature is exceeded, then an appropriate feedback signal is received at energy source 34 which then regulates the amount of energy delivered to electrode 12, as more fully explained hereafter.

Electrode 12 is coupled to an electromagnetic energy source 34 by wiring, soldering, connection to a common couplet, and the like. Electrode 12 can be independently coupled to electromagnetic energy source 34 from probes 24 and 26. Electrode 12, and probes 24 and 26 may be multiplexed so that when energy is delivered to electrode 12 it is not delivered to probes 24 and 26. Electromagnetic energy power source can be an RF source, microwave source, shortwave source, and the like.

Electrode 12 is constructed to be rigid enough so that it can be introduced percutaneously or laparoscopically through tissue without an introducer. The actual length of electrode 12 depends on the location of the selected tissue mass to be ablated, its distance from the skin, its accessibility as well as whether or not the physician chooses a laparoscopic, percutaneous or other procedure. Suitable lengths include but are not limited to 17.5 cm, 25.0 cm. and 30.0 cm. Electrode 12, can be introduced through a guide to the selected tissue ablation site.

An insulation sleeve 38 can be positioned in a surrounding relationship to an exterior surface of electrode 12. Insulation sleeve 38 can be moveable along electrode's 12 exterior surface in order to provide a variable length ablation energy delivery surface.

In one embodiment, insulation sleeve 38 can comprise a polyimide material. A sensor may be positioned on top of polyimide insulation sleeve 38. Polyamide insulation sleeve 18 is semi-rigid. The sensor can lay down substantially along the entire length of polyimide insulation sleeve 38. Handpiece 11 can serve the function of a handpiece and include markings to show the length of insulation sleeve 38 and the length of electrode's 12 exposed ablation energy delivery surface.

Referring now to FIG. 2, cap 18 is illustrated as creating a closed loop cooling medium flow channel. Cap 18 is secured to the distal ends of conduits 14 and 16 by a variety of means, including but not limited to welding, soldering, application of an epoxy, and the like. Cap 18 can have a step which is secured to the distal end of electrode 12 by soldering, welding, press sit and the like. Instead of cap 18, a "U' joint can be formed at the distal ends of conduits 16 and 18, as shown in FIG. 3.

Referring to FIG. 4, only a portion of electrode has an interface with cooling medium inlet conduit 14. However, the diameters of cooling medium inlet conduit 14 and electrode 12 are dimensioned so that a tissue interface formed adjacent to the exterior surface of electrode 12 does not become sufficiently desiccated and charred to prevent the transfer of energy through the selected tissue ablation site to the periphery of the site.

The creation of a 4 cm diameter spherical ablation is illustrated in FIG. 5. A 4 cm ablation energy delivery surface of electrode 12 is exposed. First sidewall port 20 is positioned 2 cm from a distal end of electrode 12. First probe 24 is advanced from electrode lumen with its distal end positioned at the periphery of the spherical ablation area. First sensor 28 is positioned at the distal end of first probe 24 and determines when the ablation has reached the periphery of the desired ablation area. Second sensor 30 is positioned midpoint on first probe 24 to monitor the transfer of electromagnetic energy through the desired ablation area, and determine if there are any obstructions to the ablation process at that position. Once the ablation is completed, first probe 24 is retracted back into the lumen of electrode 12.

Electromagnetic energy delivered by electrode 12 causes the electrode/tissue interface at the electrode ablation delivery surface to heat, and return the heat to electrode 12. As more heat is applied and returned, the charring effect electrode 12 increases. This can result in a loss of electromagnetic energy conductivity through the selected tissue site. The inclusion of cooling with electrode 12 does not affect the effective delivery of electromagnetic energy to the selected tissue ablation site. Cooling permits the entire selected tissue ablation site to be ablated while reducing or eliminating the heating of the electrode/tissue interface tissue.

In FIG. 6, probes 24 and 26 are each deployed out of the distal end of electrode 12 and introduced into the selected tissue mass. Probes 24 and 26 form a plane.

Figure 7:
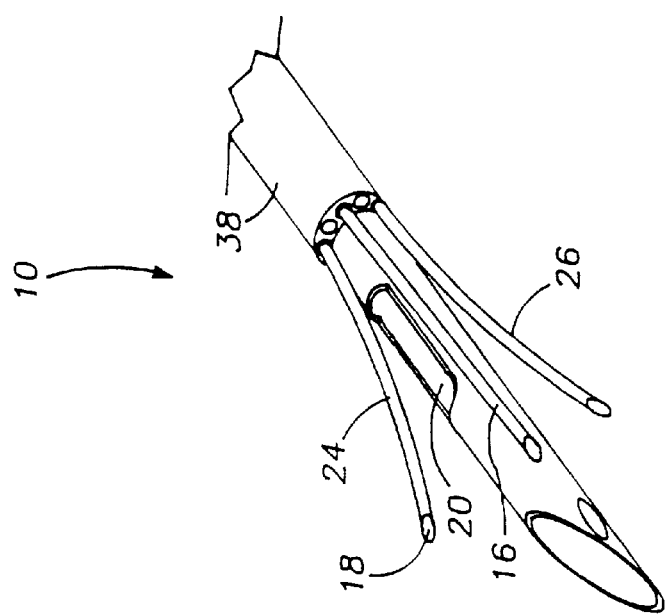
FIG. 7 is a perspective view of the distal end of the electrode of the present invention with probes extending from a distal end of an insulation sleeve.

As shown in FIG. 7 insulation sleeve 38 can include one or more lumens for receiving secondary probes 24, 26 as well as additional probes which are deployed out of a distal end of insulation sleeve 38. FIG. 8 illustrates four probes introduced out of different sidewall ports formed in the body of electrode 12. Some or all of the probes provide an anchoring function.

Figure 9:
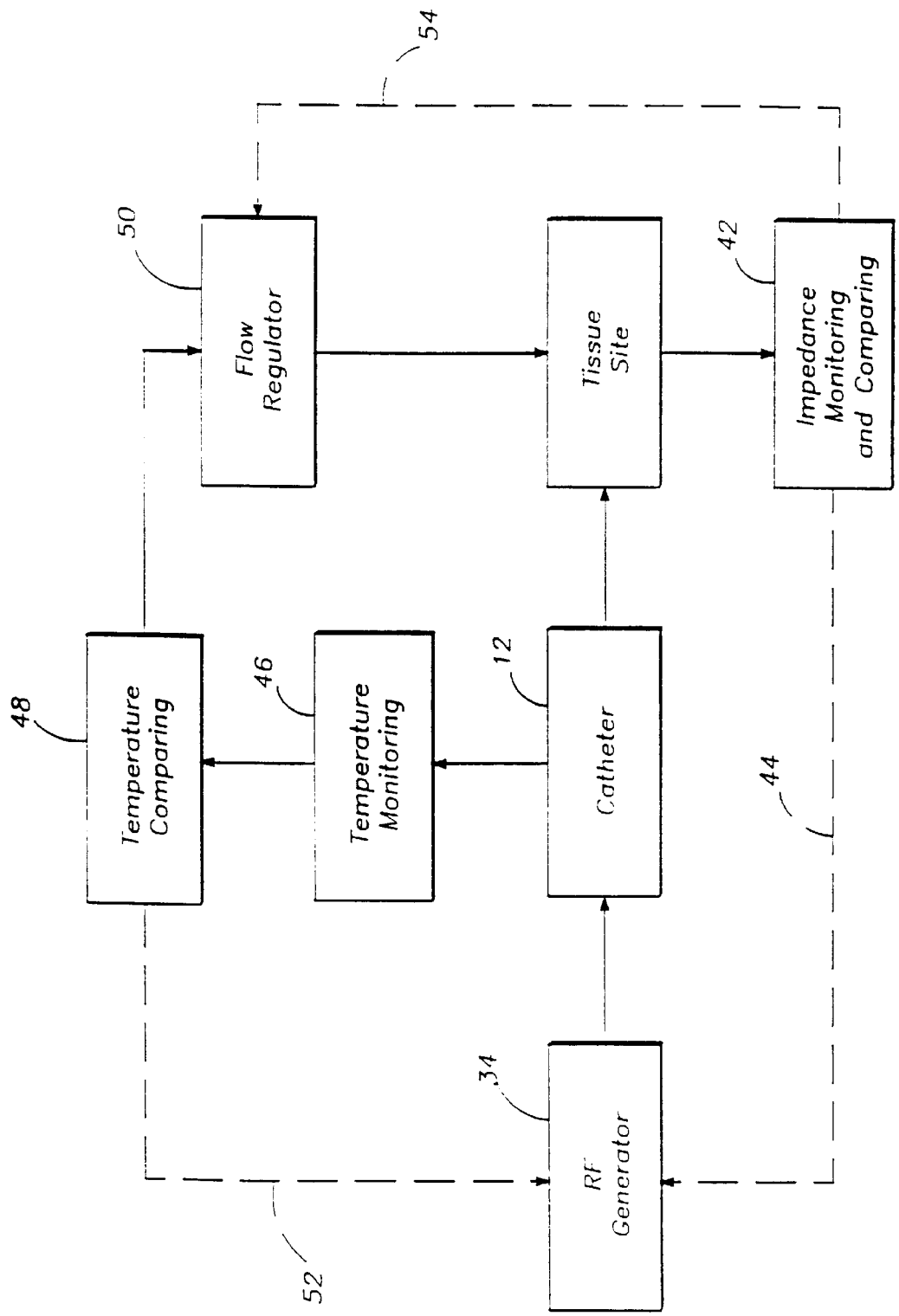
FIG. 9 is a block diagram illustrating a feedback system useful ton control the temperature of energy delivering electrodes.

FIG. 9 illustrates a block diagram of a temperature/impedance feedback system that can be used to control cooling medium flow rate through electrode 12. Electromagnetic energy is delivered to electrode 12 by energy source 34, and applied to tissue. A monitor 42 ascertains tissue impedance, based on the energy delivered to tissue, and compares the measured impedance value to a set value if the measured impedance exceeds the set value a disabling signal 44 is transmitted to energy source 34, ceasing further delivery of energy to electrode 12. If measured impedance is within acceptable limits, energy continues to be applied to the tissue. During the application of energy to tissue sensor 46 measures the temperature of tissue and/or electrode 12. A comparator 48 receives a signal representative of the measured temperature and compares this value to a pre-set signal representative of the desired temperature. Comparator 48 sends a signal to a flow regulator 50 representing a need for a higher cooling medium flow rate, if the tissue temperature is too high, or to maintain the flow rate if the temperature has not exceeded the desired temperature.

An output 52 from temperature comparator 48 can be input to energy source 34 to regulate the amount of power delivered by power source 32. Output 54 from impedance monitor 106 can be input to flow regulator 50 to regulate fluid flow and thus control temperature of the tissue.

Figure 10:
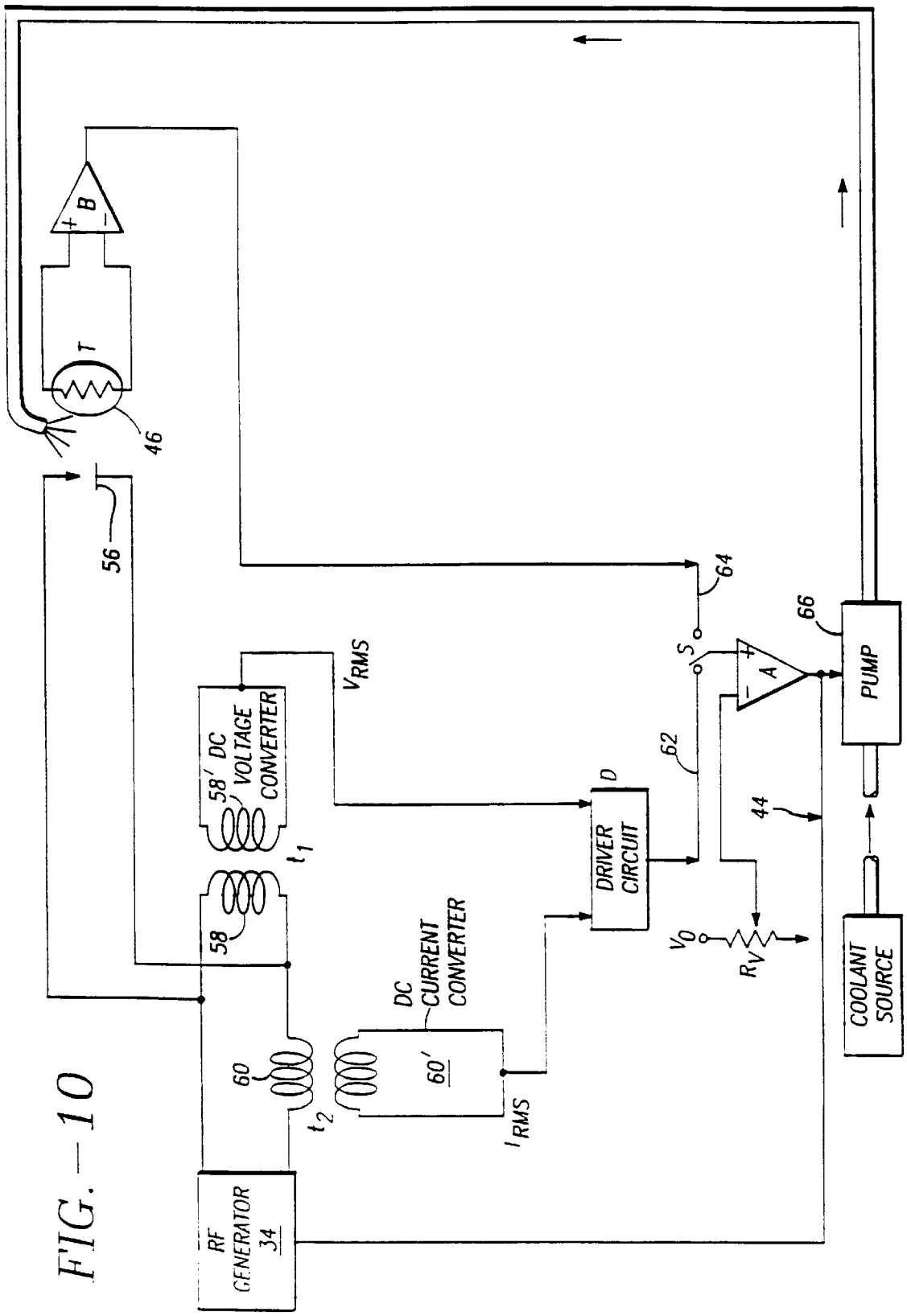
FIG. 10 illustrates a circuit useful to implement the feedback system of FIG. 9.

Referring now to FIG. 10, energy source 34 is coupled to electrode 12, to apply a biologically safe voltage to the selected tissue site. In the embodiment illustrated in FIG. 10, ablation apparatus 10 is represented as a bipolar ablation device having an energy delivering electrode 12 and a ground electrode 56. Both electrodes 12 and 56 are connected to a primary side of transformer windings 58 and 60. The common primary winding 58, 60 is magnetically coupled with a transformer core to secondary windings 58' and 60'.

The primary windings 58 of the first transformer $t_1$ couple the output voltage of ablation apparatus 10 to the secondary windings 58'. The primary windings 60 of the second transformer $t_2$ couple the output current of ablation apparatus 10 to the secondary windings 60'.

Measuring circuits determine the root mean square (RMS) values or magnitudes of the current and voltage. These values, represented as voltages, are inputted to a diving circuit D to geometrically calculate, by dividing the RMS voltage value by the RMS current value, the impedance of the tissue site at sensor 46.

The output voltage of the divider circuit D is presented at the positive (+) input terminal of comparator A. A voltage source $V_o$ supplies a voltage across the variable resistor $R_v$, thus allowing one to manually adjust the voltage presented at the negative input of comparator A. This voltage represents a maximum impedance value beyond which power will not be applied to electrode 12. Specifically, once the tissue is heated to a temperature corresponding to an impedance value greater than the maximum cut-off impedance, energy source 34 stops supplying energy to electrode 12. Comparator A can be of any of a commercially available type that is able to control the amplitude or pulse width modulation of energy source 34.

The flow rate of cooling medium can be controlled based on the tissue impedance, as represented by signal 62, or based on tissue temperature, as represented by signal 64. In one embodiment, the switch S is activated to allow the impedance signal 62 to enter the positive (+) input terminal of comparator A. This signal along with the reference voltage applied to the negative (−) input terminal actuates comparator A to produce an output signal. If the selected tissue ablation site is heated to a biologically damaging temperature, the tissue impedance will exceed a selected impedance value seen at the negative (−) input terminal, thereby generating disabling signal 44 to disable energy source 34, ceasing the power supplied to electrode 12.

The output signal of comparator A can be communicated to a pump 66. If the temperature of the selected tissue ablation site is too high, despite the tissue impedance falling within acceptable limits, pump 66 adjusts the rate of cooling medium flow applied to electrode 12 to decrease the temperature of electrode 12. The output signal of comparator A may either disable energy source's 34 energy output, depending on the tissue temperature as reflected by its impedance, or cool electrode 12 or perform both operations simultaneously.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An ablation apparatus, comprising:
    a handpiece;
    an electrode coupled to the handpiece, the electrode including a distal end sufficiently sharp to pierce tissue, a lumen, a cooling medium inlet conduit and a cooling medium exit conduit both extending at least partially through the electrode lumen, the electrode further including a port isolated from a cooling medium flowing in the inlet and outlet conduits, wherein the electrode is configured to be coupled to an energy source;
    a probe at least partially positionable in the electrode lumen, wherein the probe includes a distal portion configured to be advanced out of the port with at least one radius of curvature; and
    a thermal sensor coupled to the probe.

2. The apparatus of claim 1, wherein the cooling medium inlet and exit conduits form a closed loop at the electrode distal end.

3. The apparatus of claim 1, wherein the electrode lumen is configured to receive an infusion medium that remains isolated from the cooling medium.

4. The apparatus of claim 3, wherein the infusion medium is introduced through a proximal end of the electrode lumen to a tissue site through the port.

5. The apparatus of claim 1, further comprising:
    an advancement and retraction member coupled to the probe.

6. The apparatus of claim 1, wherein at least a portion of the probe is an electrode coupled to the energy source.

7. The apparatus of claim 1, wherein two thermal sensors are coupled to the probe.

8. The apparatus of claim 7, wherein a first thermal sensor is positioned at a distal end of the probe, and a second thermal sensor is positioned at a non-distal end location of the probe.

9. The apparatus of claim 1, wherein the thermal sensor is positioned at a distal end of the probe.

10. The apparatus of claim 1, further comprising:
    an insulation sleeve positioned around an exterior surface of the electrode.

11. The apparatus of claim 10, wherein the insulation sleeve is moveable along a longitudinal axis of the electrode.

12. The apparatus of claim 1, further comprising:
    a second port formed in the electrode.

13. The apparatus of claim 12, further comprising:
    a second probe at least partially positionable in the electrode lumen, wherein the second probe includes a distal portion configured to be advanced out of the second port with at least one radius of curvature; and
    a second thermal sensor coupled to the second probe.

14. The apparatus of claim 1, wherein the cooling medium inlet and exit conduits are constructed to add structural support to the electrode.

15. The apparatus of claim 1, wherein the probe has a distal end geometry configured to retain the electrode in a fixed position when the probe is deployed from the port.

16. The apparatus of claim 1, wherein the cooling medium inlet and exit conduits are positioned adjacent to each other in the electrode lumen.

17. The apparatus of claim 1, further comprising:
    a comparator device coupled to the thermal sensor to compare a measured temperature of a tissue site to a predetermined temperature value and generating a signal representative of a difference between the measured temperature and the predetermined temperature.

18. The apparatus of claim 17, further comprising:
    a fluid control device coupled to the inlet and outlet conduits for regulating a rate of flow of the cooling medium through the electrode lumen in response to the signal from the comparator device representative of the temperature difference to maintain the measured temperature at or below the predetermined temperature.

19. The apparatus of claim 1, further comprising:
    an energy output control device coupled to the electrode.

20. The apparatus of claim 19, wherein the energy output control device comprises:
    a impedance measuring device for measuring an impedance value of tissue based on an energy applied to the tissue;
    an impedance comparator device for comparing the measured impedance value of tissue to a predetermined maximum impedance value, the impedance comparing device generating a disabling signal if the measured impedance value exceeds the predetermined maximum impedance value; and a communication device for communicating the disabling signal to the energy source to cease further delivery of energy from the energy source to the electrode.

21. The apparatus of claim 20, further comprising:

a cooling medium control device for regulating rate of flow of cooling medium through the electrode lumen in response to the signal from the impedance comparing device representative of the impedance difference to maintain the measured impedance value at or below the predetermined maximum impedance value.

22. A method for creating an ablation volume in a selected tissue mass, comprising:

providing an ablation device including a handpiece, an electrode with a distal end, a lumen, and a sidewall port isolated from a cooling medium flowing through the electrode, a probe positionable in the electrode lumen and configured to be advanced and retracted in and out of the sidewall port and a thermal sensor supported by the probe;

inserting the electrode into the selected tissue mass;

creating a tissue interface adjacent to an electrode electromagnetic energy delivery surface;

positioning at least a portion of the probe in the electrode lumen;

advancing a distal end of the probe from the sidewall port into the selected tissue mass;

cooling at least a portion of the electrode electromagnetic energy delivery surface;

delivering electromagnetic energy from the electrode electromagnetic energy delivery surface to the selected tissue mass;

measuring temperature at a site in the selected tissue mass; and creating an ablation volume in the selected tissue mass.

23. The method of claim 22, wherein the thermal sensor is positioned at a periphery of a selected ablation volume.

24. The method of claim 22, wherein the thermal sensor is positioned between the electrode and a periphery of a selected ablation volume.

25. The method of claim 22, wherein temperature is measured at more than one location in the selected ablation volume while electromagnetic energy is delivered from the electrode.

26. The method of claim 22, wherein temperature is adjustably measured in the selected ablation volume while electromagnetic energy is delivered from the electrode.

27. The method of claim 22, wherein a second sensor is supported by the probe.

28. The method of claim 22, wherein the sensor is positioned at a distal end of the probe, and a second sensor is positioned on the probe between the distal end of the probe and an exterior surface of the electrode.

29. The method of claim 22, further comprising:

introducing an infusion medium through the aperture.

30. The method of claim 29, wherein the infusion medium is isolated from the cooling medium.

31. The method of claim 22, wherein the tissue interface is heated to a temperature exceeding 50 degrees C when electromagnetic energy is delivered to the selected tissue site.

32. The method of claim 22, wherein a deployed distal end of the probe fixes the electrode in a selected position.

33. The method of claim 22, further comprising:

measuring a temperature of the selected tissue site at the sensor;

comparing the measured temperature of the selected tissue site at the sensor to a predetermined temperature value and generating a signal representative of a difference between the measured temperature and the predetermined temperature value; and transmitting to an electromagnetic energy source coupled to the electrode a signal to cease further electromagnetic energy delivery if the measured temperature exceeds the predetermined temperature.

34. The method of claim 22, further comprising:

measuring an impedance of the selected tissue site at the sensor;

comparing the measured impedance of the selected tissue site at the sensor to a predetermined impedance value and generating a signal representative of a difference between the measured impedance and the predetermined impedance value; and transmitting to an electromagnetic energy source coupled to the electrode a signal to cease further electromagnetic energy delivery if the measured impedance exceeds the predetermined impedance value.

35. The method of claim 22, further comprising:

measuring a temperature of the selected tissue site at the sensor;

comparing the measured temperature of the selected tissue site at the sensor to a predetermined temperature value; and adjusting a flow rate of cooling medium through the electrode based on the difference between the measured temperature and the predetermined temperature value.

36. The method of claim 22, wherein a flow rate of cooling medium flowing through the inlet and outlet conduits is from 1 to 50 ml per minute.

* * * * *